(12) United States Patent
Bae et al.

(10) Patent No.: US 11,870,278 B2
(45) Date of Patent: Jan. 9, 2024

(54) IMPLANTABLE AND EXTERNAL DEVICE AND METHOD

(71) Applicant: Samsung Electronics Co., Ltd., Suwon-si (KR)

(72) Inventors: Chisung Bae, Yongin-si (KR); Joonseong Kang, Suwon-si (KR); Junyeub Suh, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 17/871,004

(22) Filed: Jul. 22, 2022

(65) Prior Publication Data

US 2023/0238835 A1 Jul. 27, 2023

(30) Foreign Application Priority Data

Jan. 12, 2022 (KR) .................. 10-2022-0004560

(51) Int. Cl.
*H02J 50/80* (2016.01)
*H02J 50/12* (2016.01)

(52) U.S. Cl.
CPC .............. *H02J 50/80* (2016.02); *H02J 50/12* (2016.02)

(58) Field of Classification Search
CPC ...................................................... H02J 50/80
USPC ....................................................... 307/104
See application file for complete search history.

(56) References Cited

U.S. PATENT DOCUMENTS

| 8,862,241 | B2 | 10/2014 | Forsell |
| 10,027,157 | B2 | 7/2018 | Labbe et al. |
| 10,652,667 | B2 | 5/2020 | Fort et al. |
| 10,873,218 | B2 | 12/2020 | Yao et al. |
| 2007/0156204 | A1 | 7/2007 | Denker et al. |
| 2010/0211133 | A1 | 8/2010 | Forsell |
| 2013/0215979 | A1 | 8/2013 | Yakovlev et al. |
| 2014/0371821 | A1 | 12/2014 | Mashiach et al. |

FOREIGN PATENT DOCUMENTS

| JP | 2015-91433 A | 5/2015 |
| KR | 10-2020-0033561 A | 3/2020 |

OTHER PUBLICATIONS

Extended European Search Report dated May 15, 2023, in Counterpart European Patent Application No. 22205286.2 (9 Pages in English).

(Continued)

*Primary Examiner* — Joseph Chang
(74) *Attorney, Agent, or Firm* — NSIP Law

(57) ABSTRACT

A device includes: a wireless power receiver configured to receive wireless power from an external device external to a body; a capacitor configured to store therein the wireless power received by the wireless power receiver; a wireless transceiver configured to transmit, to the external device, information associated with stored energy of the capacitor and scheduled energy to be used; and a processor configured to operate with the stored energy of the capacitor and process a biosignal of the body, wherein an operation of the external device and an operation of the device are synchronized, and a wireless power quantity of the wireless power to be received by the wireless power receiver from the external device is determined based on the information transmitted from the wireless transceiver to the external device.

25 Claims, 10 Drawing Sheets

(56) References Cited

OTHER PUBLICATIONS

Gutruf, et al. "Wireless, battery-free, fully implantable multimodal and multisite pacemakers for applications in small animal models." *Nature communications* vol. 10, Issue 1 (2019): pp. 1-10.
Gutruf, et al. "Fully implantable optoelectronic systems for battery-free, multimodal operation in neuroscience research." *Nature Electronics* vol. 1, Issue 12 (2018): pp. 652-660.

IMPLANTABLE AND EXTERNAL DEVICE AND METHOD

CROSS-REFERENCE TO RELATED APPLICATIONS

This application claims the benefit under 35 USC § 119(a) of Korean Patent Application No. 10-2022-0004560 filed on Jan. 12, 2022 in the Korean Intellectual Property Office, the entire disclosure of which is incorporated herein by reference for all purposes.

BACKGROUND

1. Field

The following description relates to an implantable and external device and method.

2. Description of Related Art

An electroceutical device may be implanted in a patient and provide an electrical stimulus to the nerves of the patient to treat illnesses and/or diseases of the patient. The electroceutical device may also be referred to as a neural implant or an implantable device.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a device includes: a wireless power receiver configured to receive wireless power from an external device external to a body; a capacitor configured to store therein the wireless power received by the wireless power receiver; a wireless transceiver configured to transmit, to the external device, information associated with stored energy of the capacitor and scheduled energy to be used; and a processor configured to operate with the stored energy of the capacitor and process a biosignal of the body, wherein an operation of the external device and an operation of the device are synchronized, and a wireless power quantity of the wireless power to be received by the wireless power receiver from the external device is determined based on the information transmitted from the wireless transceiver to the external device.

A first operation of the transmitting of the information by the wireless transceiver to the external device and a second operation of the receiving of the wireless power from the external device by the wireless power receiver may be synchronized.

The first operation and the second operation may be performed in a same synchronized timeslot.

For the transmitting, the wireless transceiver may be configured to transmit, to the external device, information associated with stored energy of the capacitor in a current timeslot and scheduled energy to be used based on operations to be performed in the current timeslot, and for the receiving, the wireless power receiver may be configured to receive a wireless power quantity from the external device in the current timeslot.

A time for which the wireless power receiver receives the wireless power from the external device may be determined by the external device based on the information transmitted from the wireless transceiver.

The scheduled energy may include energy to be consumed by any one or any combination of any two or more of a communicating operation of the wireless transceiver, a biosignal sensing operation, a biosignal processing operation of the processor, and an operation of applying a stimulus to the body.

The wireless power quantity may be determined based further on a state change of a wireless power link between the wireless power receiver and the external device.

The wireless power quantity may be determined such that energy remaining in the capacitor after one or more operations are performed in each timeslot corresponds to a preset reference energy.

The reference energy may be determined based on a wireless power transfer (WPT) efficiency that is based on the stored energy of the capacitor.

A wireless power link for transmitting power to the wireless power receiver may be separate from a wireless data link for transmitting information from the wireless transceiver.

The device may be a battery-free device.

The device may include either one or both of: a sensor configured to sense the biosignal of the body while the wireless power is not received from the external device; and a stimulator configured to apply a stimulus to the body while the wireless power is not received.

The device may be configured to perform initial booting based on maximum wireless power transmittable by the external device.

The device may be an implantable device.

The device may include: an implantable device comprising the wireless power receiver, the capacitor, the wireless transceiver, and the processor; and the external device, comprising: another wireless transceiver configured to receive the transmitted information; a controller configured to determine a wireless power quantity to be transmitted to the implantable device based on the received information; and a wireless power transmitter configured to transmit the determined wireless power quantity to the implantable device.

In another general aspect, a device includes: a wireless transceiver configured to receive, from an implantable device, information associated with stored energy of a capacitor comprised in the implantable device and scheduled energy to be used by the implantable device; a controller configured to determine a wireless power quantity to be transmitted to the implantable device based on the received information; and a wireless power transmitter configured to transmit the determined wireless power quantity to the implantable device, wherein an operation of the device and an operation of the implantable device are synchronized.

A first operation of the receiving of the information by the wireless transceiver from the implantable device and a second operation of the transmitting of the wireless power from the wireless power transmitter to the implantable device may be synchronized.

The controller may be configured to determine a time for transmitting the wireless power to the implantable device using the wireless power quantity determined based on the received information.

For the determining of the wireless power quantity, the controller may be configured to determine the wireless power quantity based further on a state change of a wireless power link between the wireless power transmitter and the implantable device.

The controller may be configured to Determine the wireless power quantity such that energy remaining in the capacitor after one or more operations are performed in each timeslot corresponds to a preset reference energy.

The device may be an external device external to a body.

The device may include: an external device external to a body comprising the wireless transceiver, the controller, and the wireless power transmitter; and the implantable device, comprising: a wireless power receiver configured to receive the determined wireless power quantity; a capacitor configured to store therein the wireless power received by the wireless power receiver; another wireless transceiver configured to transmit, to the external device, the information; and a processor configured to operate with the stored energy of the capacitor and process a biosignal of a body.

In another general aspect, a method of operating a device includes: transmitting, to an external device external to a body, information associated with stored energy of an internal capacitor and scheduled energy to be used; receiving wireless power from the external device and storing the received wireless power in the capacitor, in synchronization with the transmitting of the information; and sensing and processing a biosignal of the body with the stored energy of the capacitor, wherein a wireless power quantity of the wireless power to be received from the external device is determined based on the information transmitted to the external device.

In another general aspect, a method of operating a device includes: receiving, from an implantable device, information associated with stored energy of a capacitor comprised in the implantable device and scheduled energy to be used by the implantable device; determining a wireless power quantity to be transmitted to the implantable device based on the received information; and transmitting the determined wireless power quantity to the implantable device, wherein an operation of the external device and an operation of the implantable device are synchronized.

In another general aspect, a device includes: a wireless transceiver configured to receive, from another device, information associated with stored energy of a capacitor comprised in the other device and scheduled energy to be used by the other device; a controller configured to determine a length of time for transmitting wireless power to the other device, based on the received information; and a wireless power transmitter configured to transmit wireless power the other device for the determined length of time.

For the determining of the length of time, the controller may be configured to adjust the length of time from a previously determined length of time based on a comparison of a threshold to a difference between the stored energy of the capacitor and a preset reference energy.

Other features and aspects will be apparent from the following detailed description, the drawings, and the claims.

Figure 1:
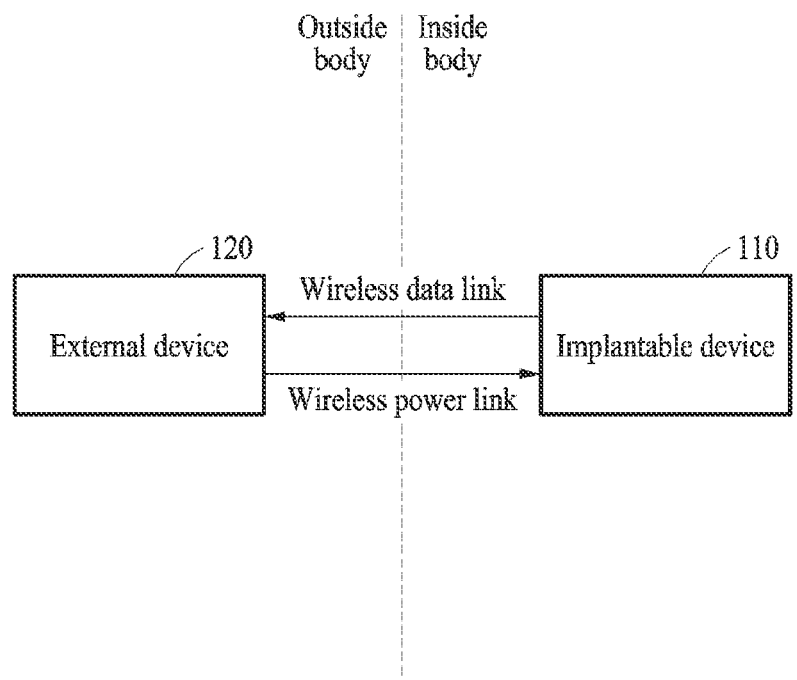
FIGS. 1 and 2 illustrate examples of an implantable device and an external device.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known, after an understanding of the disclosure of this application, may be omitted for increased clarity and conciseness.

The features described herein may be embodied in different forms and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The terminology used herein is for describing various examples only and is not to be used to limit the disclosure. The articles "a," "an," and "the" are intended to include the plural forms as well, unless the context clearly indicates otherwise. The term "and/or" includes any one and any combination of any two or more of the associated listed items. The terms "comprises," "includes," and "has" specify the presence of stated features, numbers, operations, members, elements, and/or combinations thereof, but do not preclude the presence or addition of one or more other features, numbers, operations, members, elements, and/or combinations thereof. The use of the term "may" herein with respect to an example or embodiment (for example, as to what an example or embodiment may include or implement) means that at least one example or embodiment exists where such a feature is included or implemented, while all examples are not limited thereto.

Throughout the specification, when a component is described as being "connected to," or "coupled to" another component, it may be directly "connected to," or "coupled to" the other component, or there may be one or more other components intervening therebetween. In contrast, when an element is described as being "directly connected to," or "directly coupled to" another element, there can be no other elements intervening therebetween. Likewise, similar expressions, for example, "between" and "immediately between," and "adjacent to" and "immediately adjacent to," are also to be construed in the same way. As used herein, the term "and/or" includes any one and any combination of any two or more of the associated listed items.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in the examples described herein may also be referred to as a second member, component, region, layer, or section without departing from the teachings of the examples.

Unless otherwise defined, all terms, including technical and scientific terms, used herein have the same meaning as commonly understood by one of ordinary skill in the art to which this disclosure pertains and based on an understanding of the disclosure of the present application. Terms, such as those defined in commonly used dictionaries, are to be interpreted as having a meaning that is consistent with their meaning in the context of the relevant art and the disclosure of the present application and are not to be interpreted in an idealized or overly formal sense unless expressly so defined herein.

Also, in the description of example embodiments, detailed description of structures or functions that are thereby known after an understanding of the disclosure of the present application will be omitted when it is deemed that such description will cause ambiguous interpretation of the example embodiments. Hereinafter, examples will be described in detail with reference to the accompanying drawings, and like reference numerals in the drawings refer to like elements throughout.

Figure 2:
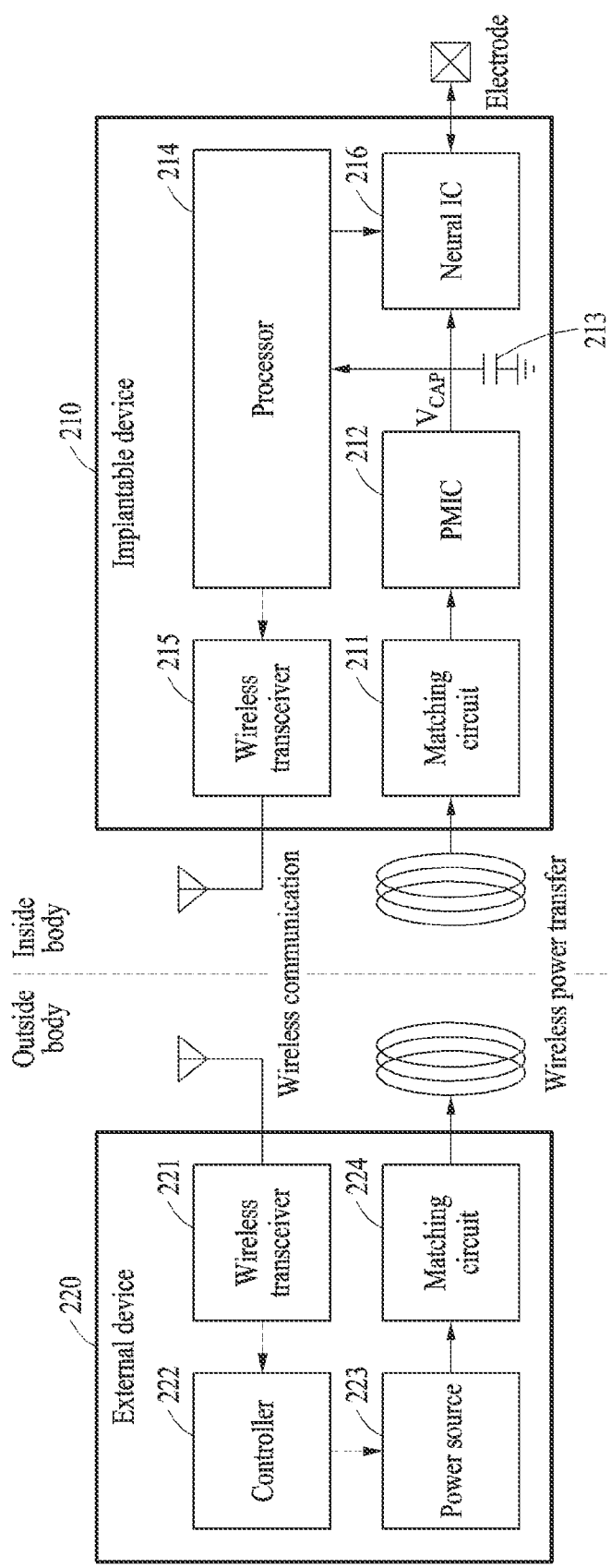

FIGS. 1 and 2 illustrate examples of an implantable device and an external device.

Referring to FIG. 1, an implantable device 110 may be an electroceutical device that is implanted in a body of a user to sense a biosignal of the user, process the sensed biosignal, and apply a stimulus to the user based on a result of the processing.

The electroceutical device may apply an electrical stimulus to nerves in a human body for treatment. The implantable device 110 may be or be used as, for example, a cochlear implant for treating a damaged cochlea, a cardiac pacemaker for treating cardiac arrhythmia, a deep brain stimulator for treating Alzheimer's or epilepsy, a spinal cord stimulator for relieving chronic spinal pains, a sacral nerve stimulator for relieving urinary incontinence, a vagus nerve stimulator for treating an autoimmune disease such as rheumatism, and/or the like, but is not limited thereto. The implantable device 110 may also be or be used as a brain-computer interface configured to perform two-way communication through a connection between a biological brain and a computer, without limitations.

The implantable device 110 may be a battery-free device that may receive wireless power from an external device 120 and store the received power in an internal capacitor, and operate with the power stored in the capacitor. With a battery not included, the implantable device 110 may be manufactured ultrasmall in size and may thus be implanted at various positions inside a body.

The external device 120 may be disposed outside (e.g., external to) the body of the user and transmit power to be used for operating the implantable device 110 through a wireless power link. The external device 120 may determine a wireless power quantity to be transmitted to the implantable device 110 based on information wirelessly received from the implantable device 110. The implantable device 110 may transmit information associated with (e.g., corresponding to) stored energy of the capacitor and scheduled energy to be used to the external device 120 through a wireless data link. The scheduled energy may refer to energy to be used for operations to be performed by the implantable device 110. The external device 120 may determine the wireless power quantity to be transmitted to the implantable device 110 based on the received information and transmit the determined wireless power quantity to the implantable device 110 through the wireless power link.

The wireless data link and the wireless power link may be independent links separate from each other. The wireless data link may be based on, for example, Bluetooth low energy (BLE), a medical implant communication system (MICS), and/or the like. When the wireless data link and the wireless power link are separate from each other, the implantable device 110 may transmit information to or receive power from the external device 120 even when the implantable device 110 is disposed deep inside the body.

A stable operation of the implantable device 110 without a battery may result from performing wireless power transfer robustly against a channel change of the wireless power link, transmitting a power quantity not exceeding a determined quantity (e.g., to prevent a temperature of the implantable device 110 from being out of a determined allowable range and prevent neighboring tissues from being damaged), and preventing electromagnetic waves occurring due to wireless power transfer or wireless data transfer from exceeding a specific absorption rate (SAR) which is a regulated rate for the absorption of electromagnetic waves. Non-limiting examples of such operations for the stable operation of the implantable device 110 will be described in detail with reference to the accompanying drawings.

Referring to FIG. 2, an implantable device 210 (the implantable device 110 of FIG. 1, as a non-limiting example) may transmit information to be used for a stable operation to an implantable device 210 at preset time intervals, and an external device 220 (the external device 120 of FIG. 1, as a non-limiting example) may calculate and provide a determined power quantity of the implantable device 210. The implantable device 210 and the external device 220 may synchronize a timeslot that is a working unit time through wireless communication. For the external device 220, the working unit time may correspond to a time interval for adjusting wireless power control. For the implantable device 210, the working unit time may correspond to a scheduling time interval for repeating wireless communication with the external device 220 and electroceutical functions (e.g., biosignal sensing, biosignal processing, and stimulus applying).

The implantable device 210 may include a matching circuit 211, a power management integrated circuit (PMIC) 212, a capacitor 213, a processor 214 (e.g., one or more processors), a wireless transceiver 215, and a neural integrated circuit (IC) 216.

The matching circuit 211 may be configured to match a resonant frequency of a coil antenna for wireless power reception and a receiving impedance, and the PMIC 212 may be configured to convert, into a constant voltage, power received by a rectifier and a direct current (DC)-to-DC or low dropout (LDO) converter. The matching circuit 211 and the PMIC 212 may collectively be referred to herein as a wireless power receiver for the convenience of description.

The capacitor 213 may store therein power received through the wireless power receiver. A current voltage of the capacitor 213 may be indicated herein as $V_{CAP}$ or $V_C$. The capacitor 213 may be or include an energy storage device having a fast charging and discharging rate, such as, for example, a general capacitor, a supercapacitor, a small battery, and/or a thin-film battery.

The processor 214 may operate with energy stored in the capacitor 213 and process a biosignal sensed by a sensor (e.g., a sensor of the neural IC 216). The processor 214 may monitor a neural signal activity through the neural IC 216 and/or determine whether to apply a stimulus to a nerve. The processor 214 may determine information associated with the current voltage $V_{CAP}$ stored in the capacitor 213 and with energy to be used for operations to be performed in a current (e.g., present) timeslot, and transmit the information to the external device 220 through the wireless transceiver 215. The energy to be used for operations to be performed in a timeslot may also be referred to herein as scheduled energy to be used for the operations.

The wireless transceiver 215 may transmit the information determined by the processor 214 to the external device 220 through wireless communication. The wireless communication may be performed based on, for example, BLE, MICS, and/or the like.

The neural IC 216 may sense a biosignal using the sensor of the neural IC 216 and apply a stimulus using a stimulator of the neural IC 216, through an electrode. For the convenience of description, the neural IC 216 may be used as a collective term referring to a sensor configured to sense a biosignal and a stimulator configured to apply a stimulus.

The external device 220 may include a wireless transceiver 221, a controller 222 (e.g., one or more processors), a power source 223, and a matching circuit 224.

The wireless transceiver 221 may receive the information transmitted from the wireless transceiver 215 of the implantable device 210.

The controller 222 may determine a wireless power quantity to be transmitted to the implantable device 210 in a current timeslot based on the information received by the wireless transceiver 221. For example, the controller 222 may determine a wireless power quantity that will result in the capacitor 213 having a preset reference voltage after the implantable device 210 performs an operation scheduled in the current timeslot, based on stored energy of the capacitor 213 and scheduled energy to be used by the implantable device 210 to perform the operation scheduled in the current timeslot.

The power source 223 may be configured to supply power and include, for example, a wired power source and/or a battery. The matching circuit 224 may be configured to match a resonant frequency of a coil antenna for wireless power transfer and a transmitting impedance. The power source 223 and the matching circuit 224 may be collectively referred to herein as a wireless power transmitter for the convenience of description.

The external device 220 may start wireless power transfer to the implantable device 210 at a start point of each timeslot.

The external device 220 may start wireless power transfer to the implantable device 210 at a start point of each timeslot. The implantable device 210 may transmit, to the external device 220, information associated with stored energy of the capacitor 213 at a start point of a current timeslot and scheduled energy to be used in the current timeslot. The external device 220 may determine an energy quantity to be transmitted in the current timeslot based on the information transmitted from the implantable device 210, and determine a time for performing wireless power transfer based on the determined energy quantity. For example, the time for performing wireless power transfer may be proportional to the energy quantity to be transmitted, but is not limited thereto.

As described above, after synchronization of the implantable device 210 and the external device 220, calculating energy to be used for a specific time interval (e.g., a timeslot) and transmitting the calculated energy to the implantable device 210 may result in the implantable device 210 operating stably despite a sudden change of a load current by an operation (e.g., electrostimulation, neural recording, data transfer, etc.) performed by the implantable device 210. In addition, transmitting only an energy quantity determined as necessary for the implantable device 210 may prevent the implantable device 210 from being heated by excessive energy transferred and control electromagnetic waves radiated by the external device 220 not to exceed a SAR level.

FIGS. 3 through 7 illustrate examples of a closed-loop power control operation for an implantable device.

Figure 3:
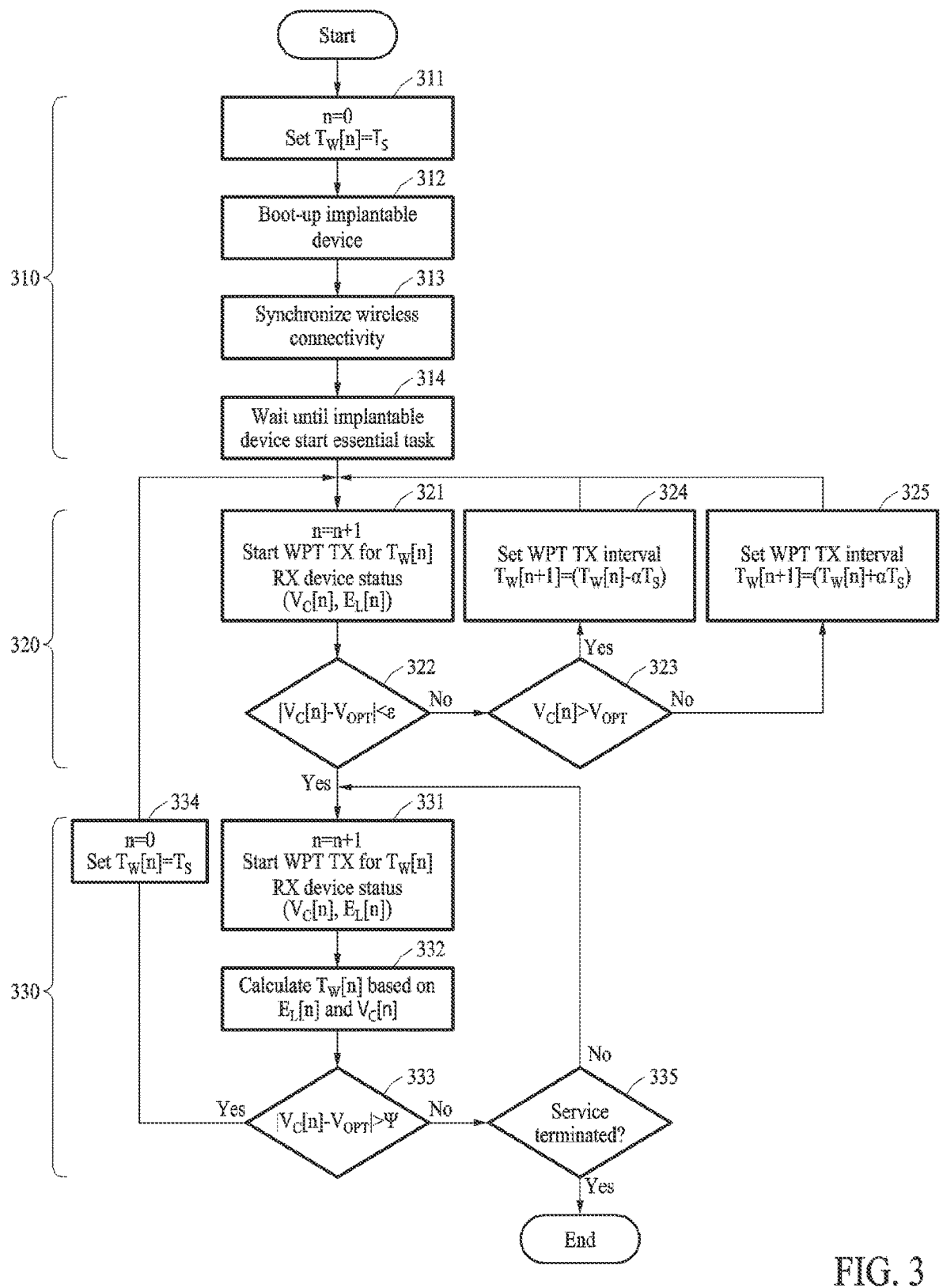
FIGS. 3 through 7 illustrate examples of a closed-loop power control operation for an implantable device.

Referring to FIG. 3, a closed-loop power control operation for an implantable device may be divided into three stages including a first stage 310, a second stage 320, and a third stage 330.

The first stage 310 may be an initial booting stage.

In operation 311, when a great power quantity is to be used to initially boot the implantable device, an external device may transmit maximum wireless power to the implantable device without controlling power. In operation 311, n denotes an index of a timeslot, $T_W[n]$ denotes a time for (e.g., a length of time during) which wireless power transfer is performed in an nth timeslot, and $T_S$ denotes a length of one timeslot. For example, n being (n=0) may indicate initialization of an index of a timeslot. In addition, $T_W[n]$ being ($T_W[n]=T_S$) may indicate that the time for which wireless power transfer is performed in the nth timeslot corresponds to an entire length of the timeslot, and that wireless power transfer is continuously performed in the timeslot.

In operation 312, the implantable device may perform initial booting based on the wireless power received from the external device. The implantable device may store energy received from the external device in a capacitor, and perform (e.g., a processor of the implantable device may perform) the booting based on the energy stored in the capacitor.

In operation 313, when a power source is turned on, the implantable device may synchronize a timeslot which is a working unit time, using wireless communication with the external device.

In operation 314, the implantable device may receive the maximum wireless power from the external device until it starts an essential task. The essential task may include, for example, measuring and/or processing a biosignal of a user, and further may include applying a stimulus according to examples.

The second stage 320 may be a steady state searching stage. In the second stage 320, a time for which wireless power is transmitted from the external device to the implantable device in a timeslot may be adjusted, and a steady state in which energy stored in the implantable device becomes steady may be searched. The second stage 320 may start when a notification that the booting is completed after the timeslot is synchronized and the essential task is activated in the first stage 310 is provided to the external device. In the second stage 320, the essential task may be performed in each timeslot.

In operation 321, in a new timeslot, the external device may transmit wireless power to the implantable device for a time $T_W[n]$, and the implantable device may transmit state information (e.g., a voltage $V_C[n]$ of the capacitor and scheduled energy $E_L[n]$) to the external device. In this case, $T_W[n]$ may be set as $T_S$ in operation 311, and thus wireless power transfer may be performed in an entire timeslot interval. The voltage $V_C[n]$ of the capacitor may correspond to information associated with stored energy of the capacitor in a current timeslot, and the stored energy of the capacitor may be determined from the voltage $V_C[n]$.

In operation 322, the external device may determine whether a difference between the voltage $V_C[n]$ of the capacitor and a preset reference voltage $V_{OPT}$ is less than a first threshold $\varepsilon$. The preset reference voltage $V_{OPT}$ may be a voltage of the capacitor at which a wireless power transfer efficiency is optimized. The wireless power transfer efficiency may vary based on the stored energy of the capacitor, and the reference voltage $V_{OPT}$ may be determined to be a voltage corresponding to the stored energy of the capacitor having an optimal wireless power transfer efficiency. The first threshold $\varepsilon$ may be determined to be a value that is greater than a measurement error of the voltage $V_C[n]$ of the capacitor and is sufficiently smaller than the voltage $V_C[n]$ of the capacitor, which may prevent a result of the determining in operation 322 from changing due to the measurement error.

When a great wireless power quantity is transmitted for initial booting, the difference between the voltage $V_C[n]$ of the capacitor and the preset reference voltage $V_{OPT}$ may be greater than the first threshold $\varepsilon$, and thus operation 323 may then be performed.

In operation 323, the external device may determine whether the voltage $V_C[n]$ of the capacitor is greater than the preset reference voltage $V_{OPT}$. When a great wireless power quantity is transmitted for initial booting, the voltage $V_C[n]$ of the capacitor may be greater than the preset reference voltage $V_{OPT}$, and thus operation 324 may then be performed.

In operation 324, the external device may determine a wireless power transfer time $T_W[n+1]$ of a subsequent timeslot to be $T_W[n]-\alpha T_S$. In this case, a may be a factor for adjusting $T_W[n+1]$ for each timeslot. For example, when the factor is set as 0.1, $T_W[n+1]$ may be adjusted to be 10% of $T_S$ in size. However, a value of a is not limited to the foregoing example and may set to be various values according to a situation and determined need. When $T_W[n+1]$ is set, operation 321 may be performed again.

When the voltage $V_C[n]$ of the capacitor becomes less than the reference voltage $V_{OPT}$ as operations 321 through 324 are performed repeatedly, operation 325 may then be performed. When the voltage $V_C[n]$ of the capacitor is equal to the reference voltage $V_{OPT}$, operation 331 may be performed after operation 322, and thus such a case when the voltage $V_C[n]$ of the capacitor is equal to the reference voltage $V_{OPT}$ may not be considered in operation 323.

In operation 325, the external device may determine the wireless power transfer time $T_W[n+1]$ of the subsequent timeslot to be $T_W[n]+\alpha T_S$. This may be a case where the voltage $V_C[n]$ of the capacitor is less than the reference voltage $V_{OPT}$, and thus the wireless power transfer time $T_W[n+1]$ of the subsequent timeslot may increase by a predetermined size.

By causing the voltage $V_C[n]$ of the capacitor to converge on the preset reference voltage $V_{OPT}$ through a hill-climbing technique based on operations 321, 322, 323, 324, and 325 (e.g., the second stage 320), the steady state in which the voltage $V_C[n]$ of the capacitor becomes significantly similar to or the same as the reference voltage $V_{OPT}$ may be reached. In the steady state, energy used in the implantable device may correspond to energy provided by the external device to the implantable device.

In a process of reaching the steady state in the second stage 320, wireless power transfer and received energy may be represented by Equation 1 below, for example.

$$\eta \times (P_{WPT} \times T_{WPT\_IDLE}) = E_{RX\_IDLE} = (E_{BLE} + E_{SENS} + E_{PRC})$$ Equation 1:

In Equation 1, $\eta$ denotes an end-to-end power conversion efficiency, $P_{WPT}$ denotes instantaneous peak power transmitted from the external device, and $T_{WPT\_IDLE}$ denotes a wireless power transfer time in the steady state. $P_{WPT} \times T_{WPT\_IDLE}$ denotes a wireless power quantity to be transmitted, i.e., wireless power transfer energy. $E_{RX\_IDLE}$ denotes received energy of the implantable device and may be determined to be a sum of energy to be used to perform essential tasks. That is, $E_{RX\_IDLE}$ may be determined to be a sum of wireless communication energy $E_{BLE}$, biosignal sensing energy $E_{SENS}$, and biosignal processing energy $E_{PRC}$. In the steady state, values of variables, except for $\eta$, may be known, and thus a value of $\eta$ may be determined. As described above, $\eta$ may denote the end-to-end power conversion efficiency that varies according to a wireless power transfer distance or a wireless power link state.

When the steady state in which the difference between the voltage $V_C[n]$ of the capacitor and the preset reference voltage $V_{OPT}$ is less than the first threshold value $\varepsilon$ is determined to be reached in operation 322 in the second stage 320, the third stage 330 may then be performed. In the third stage 330, the closed-loop wireless power control may be performed.

In operation 331, in a new timeslot, the external device may start an operation of transmitting wireless power to the implantable device for a time $T_W[n]$, and the implantable device may transmit state information (e.g., the voltage $V_C[n]$ of the capacitor and the scheduled energy $E_L[n]$) to the external device.

In operation 332, the external device may determine the time $T_W[n]$ for which the wireless power is transmitted to the implantable device in a current timeslot based on the state information transmitted from the implantable device. The external device may determine the time $T_W[n]$ for which the wireless power is transmitted in the current timeslot based on energy stored in the implantable device in the current timeslot and energy scheduled to be used for operations (e.g., any one or any combination of any two or more of wireless communication, biosignal sensing, biosignal processing, and stimulus applying) to be performed in the current timeslot. The external device may thereby cause the voltage $V_C[n]$ of the capacitor to be maintained at $V_{OPT}$ at an end point of the timeslot.

The external device may determine $T_W[n]$ as represented by Equation 2 below, for example.

$$T_W[n] = T_{WPT\_IDLE}/E_{RX\_IDLE} \times \{E_L[n] + C/2(V_{OPT}^2 - V_C[n]^2)\}$$ Equation 2:

In Equation 2, $E_L[n]$ denotes scheduled energy that is determined based on operations to be performed in an nth timeslot and may be the same as $E_{RX\_IDLE}$ in the steady state. C denotes capacitance of the capacitor configured to store energy in the implantable device. $C/2(V_{OPT}^2 - V_C[n]^2)$ denotes compensated energy by a change in a wireless power link. For example, when a distance between the external device and the implantable device increases, a wireless power transfer efficiency may decrease, and thus the external device may transmit a greater wireless power quantity. Thus, the increased wireless power quantity may be represented by $C/2(V_{OPT}^2 - V_C[n]^2)$.

In operation 333, whether the difference between the voltage $V_C[n]$ of the capacitor and the preset reference voltage $V_{OPT}$ is greater than a second threshold value $\psi$ may be determined. The second threshold value $\psi$ may be a reference used for determining whether the voltage $V_C[n]$ of the capacitor is the same as or significantly similar to the preset reference voltage $V_{OPT}$, and may be set to be the same as or different from the first threshold $\varepsilon$.

When the difference between the voltage $V_C[n]$ of the capacitor and the preset reference voltage $V_{OPT}$ is greater than the second threshold value $\psi$, it may be determined that the closed-loop power control in the third stage 330 is out of a range, and the second stage 320 may be performed again after initialization (i.e., n=0 and $T_W[n]=T_S$) is performed in operation 334.

When the difference between the voltage $V_C[n]$ of the capacitor and the preset reference voltage $V_{OPT}$ is less than or equal to the second threshold value $\psi$, operation 335 may then be performed. In operation 335, whether a service is terminated may be determined. For example, when operations of the implantable device are no longer to be performed or determined to no longer be needed, the service may be determined to be terminated. When the service is not terminated, operation 331 may then be performed.

Figure 4:
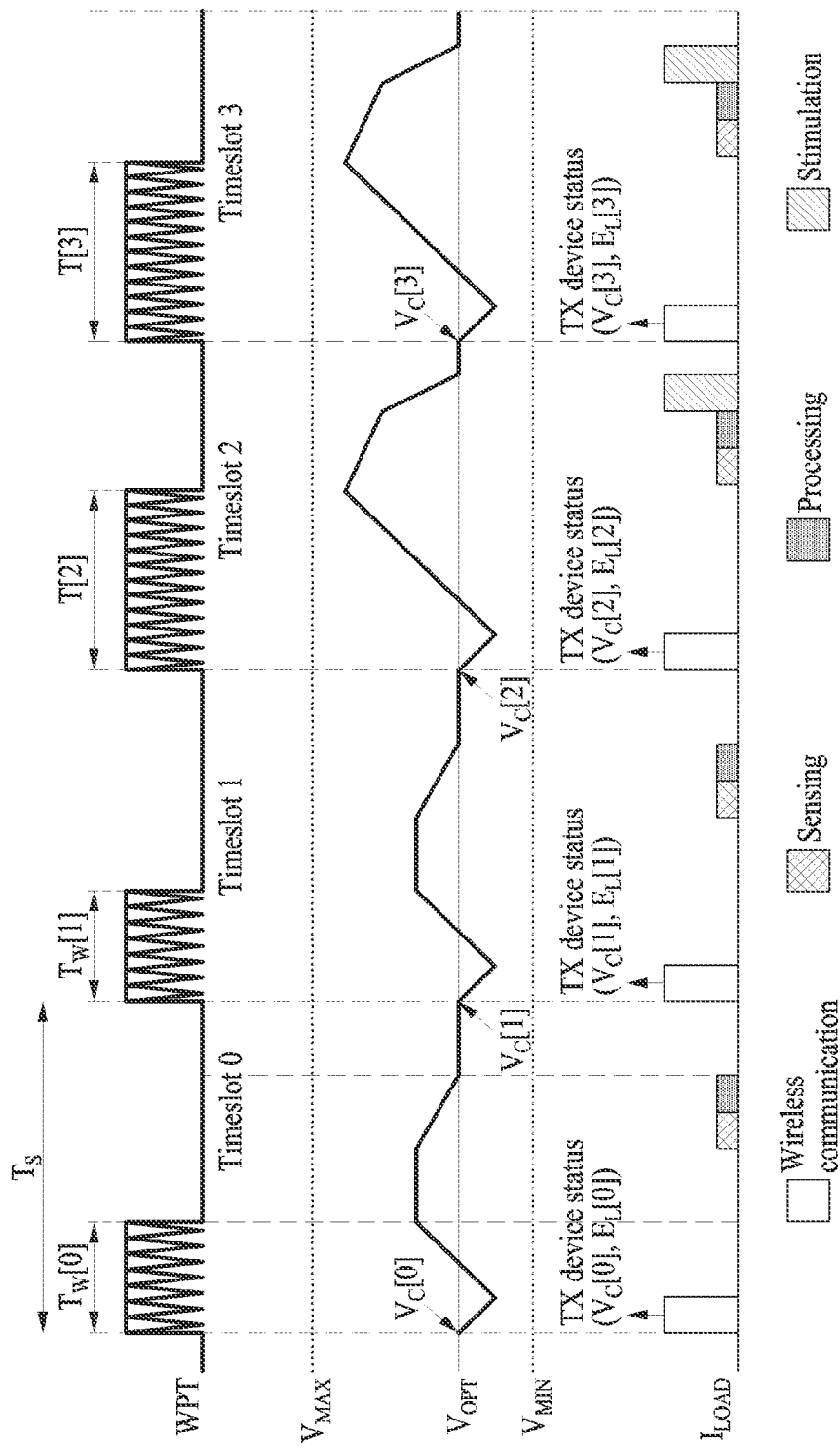

FIG. 4 is a timing diagram illustrating operations performed by an implantable device and an external device based on a closed-loop power control operation. The timing diagram may illustrate operations performed in the third stage 330 described above with reference to FIG. 3, for example.

In the example of FIG. 4, WPT denotes power transmitted by the external device, $V_{MAX}$ denotes a maximum voltage of a capacitor in the implantable device, and $V_{MIN}$ denotes a minimum voltage of the capacitor. $V_C[n]$ denotes a voltage of the capacitor at a start point of an nth timeslot. Referring to a graph in FIG. 4, when a current voltage $V_{CAP}$ of the capacitor decreases to be less than $V_{MIN}$, a system failure may occur. $I_{LOAD}$ denotes a current consumed by an operation performed by the implantable device, and an average consumed current of the implantable device in the nth timeslot may be denoted as $I_L[n]$. The average consumed current $I_L[n]$ may correspond to energy $E_L(n)$ scheduled to be used in the nth timeslot. The energy $E_L(n)$ scheduled to be used may also be referred to herein as scheduled energy $E_L(n)$.

As described above, closed-loop wireless power control may operate in a timeslot-based manner. The external device may start wireless power transfer to the implantable device at a start point of each timeslot, and the implantable device may transmit information associated with the voltage $V_C[n]$ of the capacitor and the scheduled energy $E_L[n]$ for a corresponding timeslot to the external device. Wireless communication may also consume energy, and thus the voltage $V_{CAP}$ of the internal capacitor may decrease during wireless communication performed by the implantable device. However, when wireless communication is completed, the voltage $V_{CAP}$ of the capacitor may increase again by a wireless power quantity transmitted from the external device. The external device may determine a wireless power transfer time $T_W[n]$ in a current timeslot based on the information received from the implantable device.

When wireless power transfer is completed, the implantable device may sense and process a biosignal (e.g., a neural signal) with energy stored in the capacitor, and additionally apply a stimulus as determined as needed. When the external device transmits wireless power, high energy may radiate in a specific frequency band (e.g., 13.56 megahertz (MHz)), which may act as noise in measuring a biosignal and applying a stimulus by the implantable device. Thus, the implantable device of one or more embodiments may measure a biosignal and apply a stimulus after wireless power transfer is completed, thereby improving the quality of a sensed signal and minimizing the distortion of a nerve stimulating wave.

Figure 5:
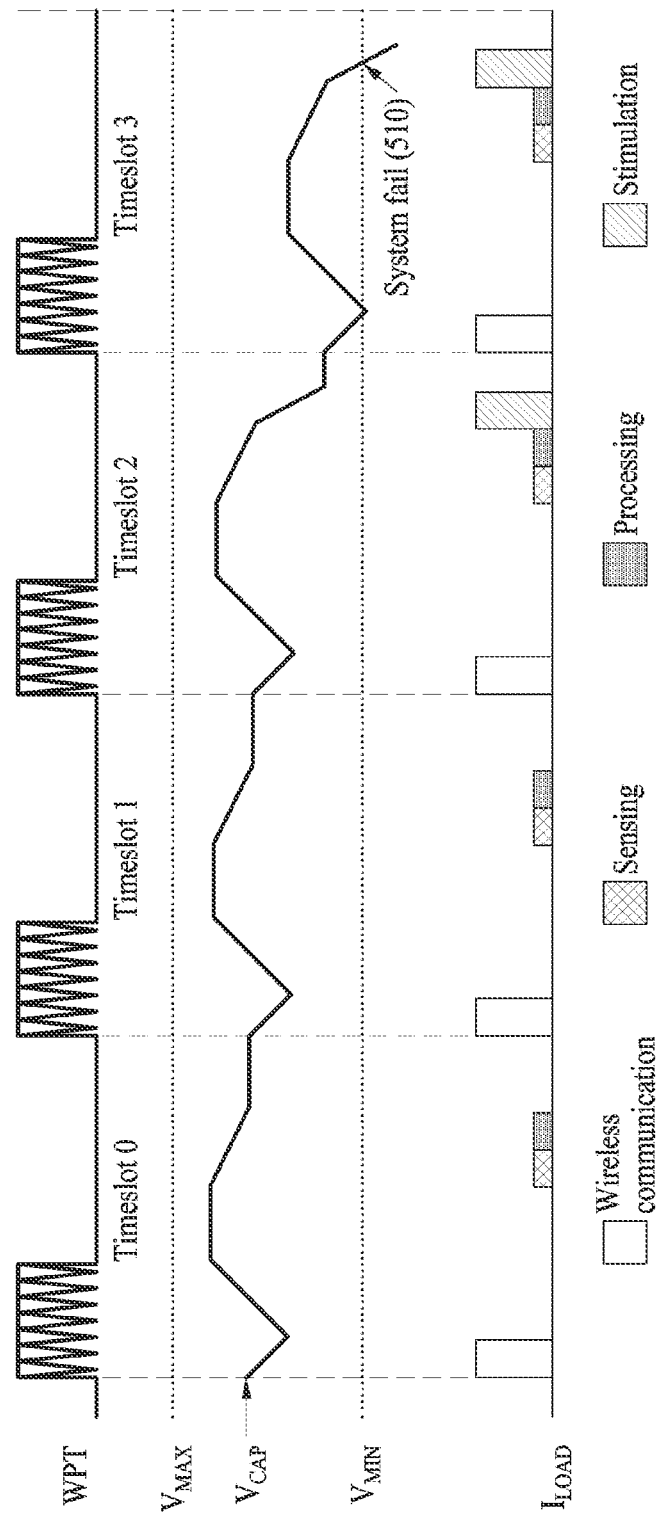

FIG. 5 illustrates an example of transmitting a preset wireless power quantity from a typical external device without consideration of a state of an implantable device. In a case in which the typical external device transmits only a preset wireless power quantity to the implantable device, the implantable device may lack available energy when the implantable device performs an operation that increases a load current, for example, when performing multi-channel neural signal measurement or electrical stimulation, and a voltage of a capacitor may drop to be a minimum voltage $V_{MIN}$ or less and a system failure 510 may then occur. Accordingly, in contrast to the typical device, the device of one or more embodiments may perform the closed-loop power control described above with reference to FIGS. 1-4, and the device of one or more embodiments may effectively prevent the system failure 510 from occurring by determining a wireless power quantity to be transmitted to the implantable device based on stored energy of the implantable device and scheduled energy to be used.

Figure 6:
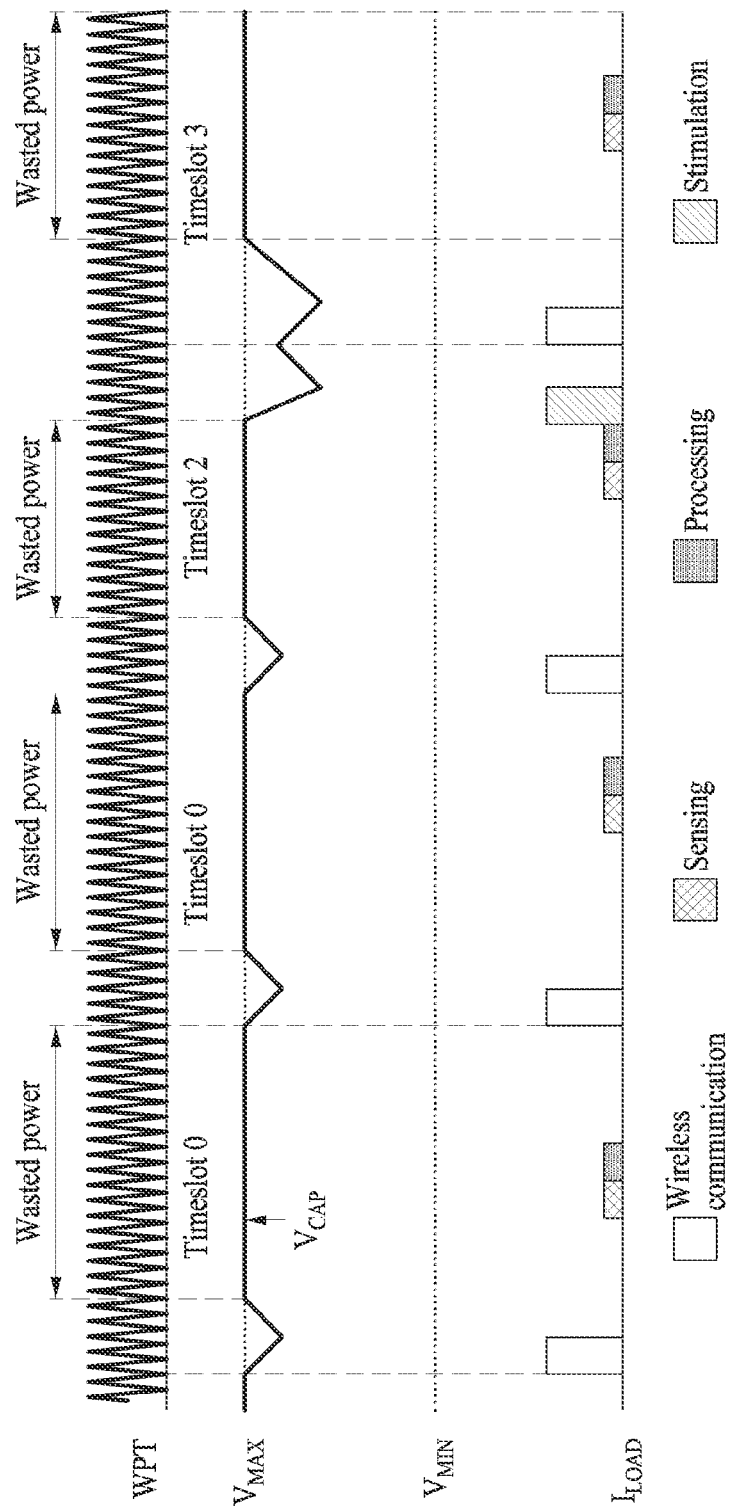

FIG. 6 illustrates an example of transmitting a maximum wireless power quantity from a typical external device to an implantable device. When the typical external device transmits a maximum wireless power quantity to the implantable device, a destructively high quantity of energy may be transmitted when a load current of the implantable device is small. This high quantity of energy may induce a heat rise in the implantable device, thereby doing damage to surrounding cells. Accordingly, in contrast to the typical device, the device of one or more embodiments may perform the closed-loop power control described above with reference to FIGS. 1-4, and the device of one or more embodiments may effectively prevent the surrounding cells from being damaged by the heat rise due to the high quantity of energy by determining a wireless power quantity to be transmitted to the implantable device based on stored energy of the implantable device and scheduled energy to be used.

Figure 7:
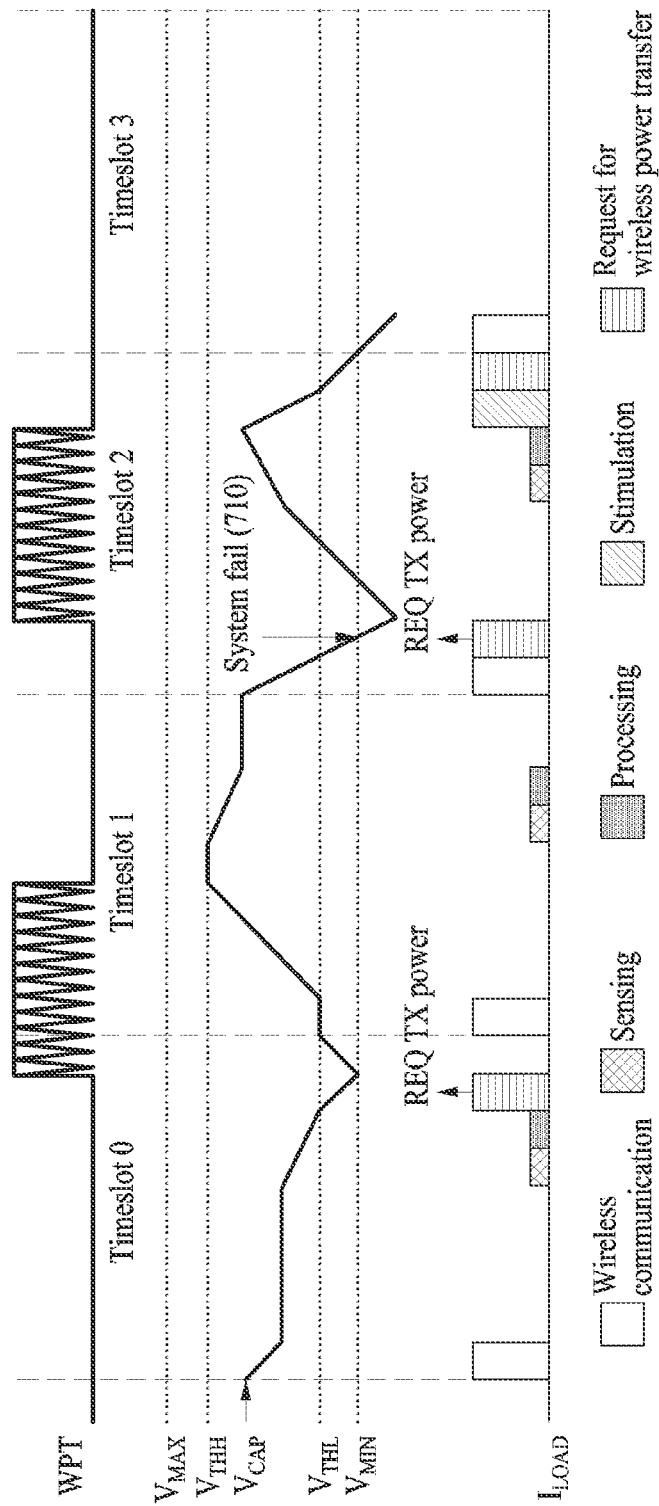

FIG. 7 illustrates an example of a closed-loop power control operation performed without synchronization of a typical implantable device and a typical external device. When a voltage of a capacitor becomes less than a first threshold voltage $V_{THL}$ without the synchronization of the typical implantable device and the typical external device, the implantable device may request wireless power transfer through wireless communication. In general, at least few milliamperes (mA) of current may be consumed for wireless communication. Thus, when the typical implantable device frequently requests wireless power transfer due to an increase in a load current, a failure-inducing quantity of energy may be consumed thereby. For example, when the request for wireless power transfer by the typical implantable device overlaps the application of a stimulus and a high peak current is thus consumed, the voltage of the capacitor may decrease to a minimum voltage $V_{MIN}$ or less and a system failure 710 may occur thereby. Accordingly, in contrast to the typical device, the device of one or more embodiments may perform the synchronized closed-loop power control described above with reference to FIGS. 1-4, and the device of one or more embodiments may effectively prevent the system failure 710 from occurring by determining a wireless power quantity to be transmitted to the implantable device based on stored energy of the implantable device and scheduled energy to be used for each timeslot.

Figure 8:
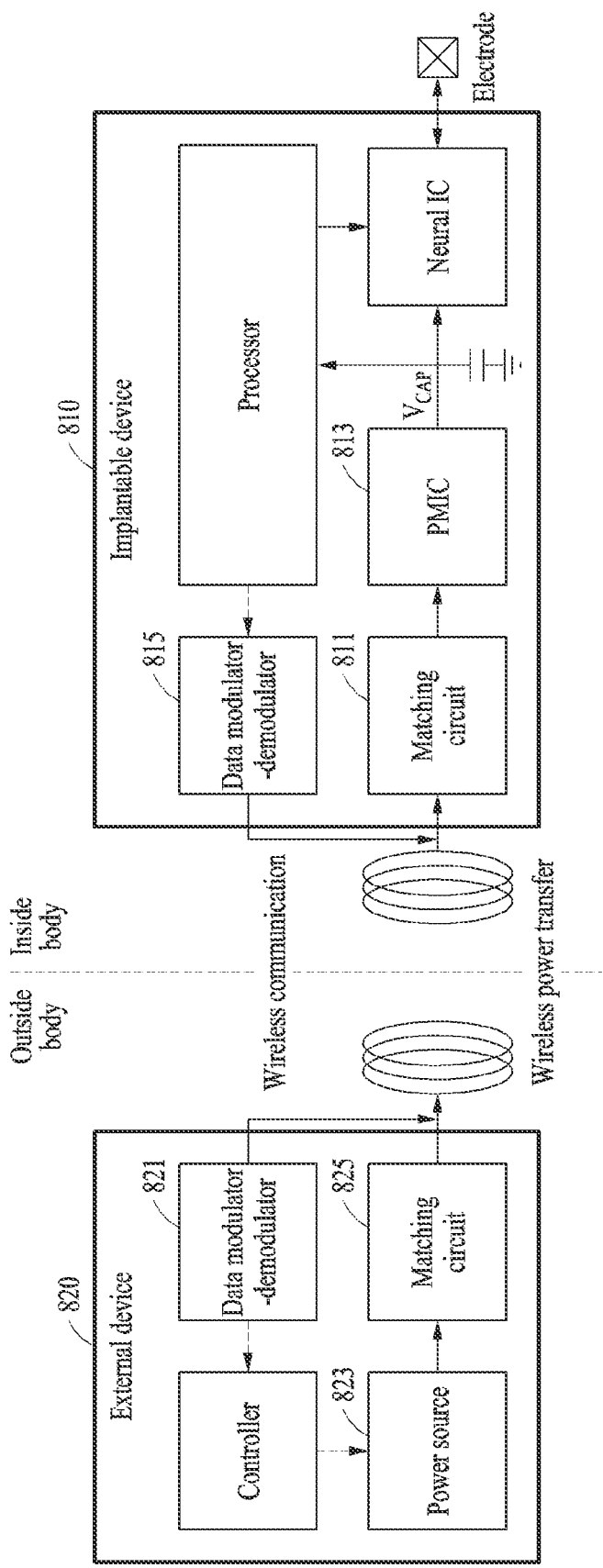
FIG. 8 illustrates an example of an implantable device and an external device.

FIG. 8 illustrates an example of an implantable device and an external device.

Referring to FIG. 8, an implantable device 810 (the implantable device 110 of FIG. 1, as a non-limiting example) and an external device 820 (the external device 120 of FIG. 1, as a non-limiting example) may perform wireless communication and wireless power transfer based on near-field communication (NFC).

Wireless power transfer may be performed through a matching circuit 811 and a PMIC 813 of the implantable device 810 and a power source 823 and a matching circuit 825 of the external device 820. For the convenience of description, the matching circuit 811 and the PMIC 813 may be collectively referred to herein as a wireless power receiver, and the power source 823 and the matching circuit 825 may be collectively referred to herein as a wireless power transmitter. Wireless communication may be performed through a data modulator-demodulator 815 of the implantable device 810 and a data modulator-demodulator 821 of the external device 820.

For a more detailed description, reference may be made to what has been described above with reference to FIG. 2.

Figure 9:
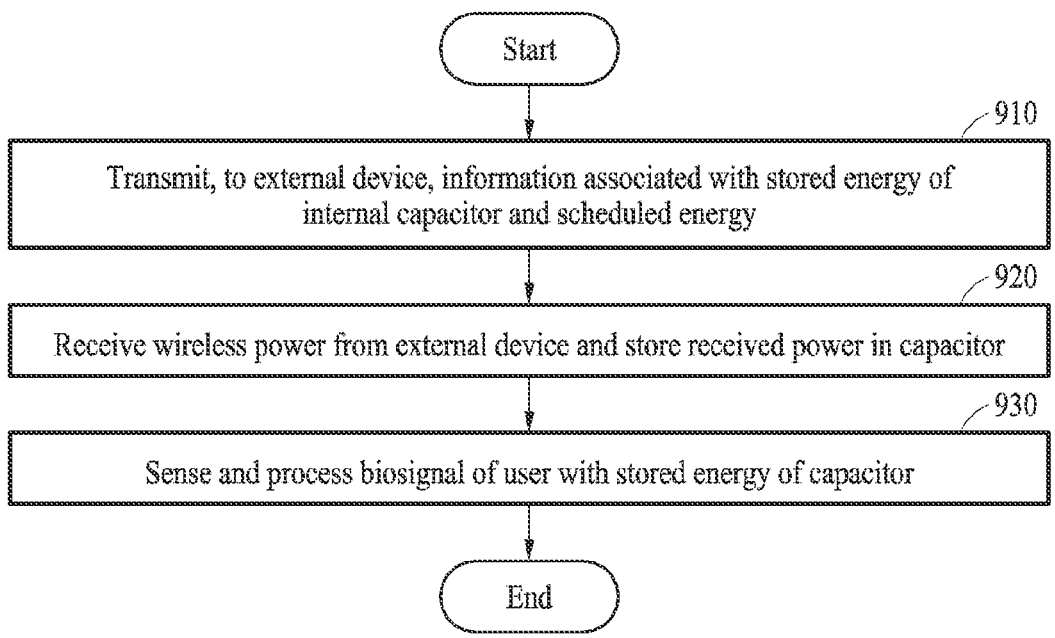
FIG. 9 illustrates an example of a method of operating an implantable device.

FIG. 9 illustrates an example of a method of operating an implantable device.

Operations to be described hereinafter may be performed in sequential order, but not be necessarily performed in sequential order. For example, the order of the operations may change, and any one or any combination of any two or more of the operations may be performed in parallel. Operations 910 through 930 to be described hereinafter with reference to FIG. 9 may be performed by one or more components of an implantable device described herein.

In operation 910, the implantable device may transmit, to an external device, information associated with stored energy of an internal capacitor and scheduled energy to be used. In operation 920, the implantable device may receive wireless power from the external device and store the received power in the capacitor, in synchronization with operation 910 of transmitting the information. A wireless power quantity to be received by the implantable device from the external device may be determined based on the information transmitted to the external device. In operation 930, the implantable device may sense and process a biosignal of a user with the stored energy of the capacitor.

For a detailed description of the operations described with reference to FIG. 9, reference may be made to what has been described above with reference to FIGS. 1 through 8.

Figure 10:
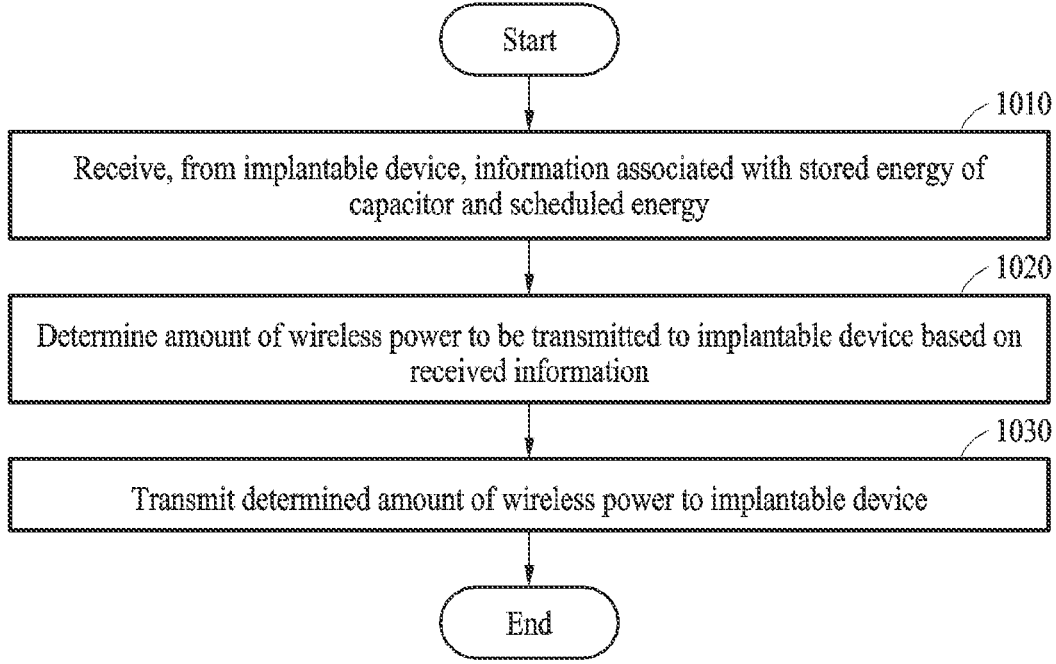
FIG. 10 illustrates an example of a method of operating an external device.

FIG. 10 illustrates an example of a method of operating an external device.

Operations to be described hereinafter may be performed in sequential order, but not be necessarily performed in sequential order. For example, the order of the operations may change, and any one or any combination of any two or more of the operations may be performed in parallel. Operations 1010 through 1030 to be described hereinafter with reference to FIG. 10 may be performed by one or more components of an external device described herein.

In operation 1010, the external device may receive, from an implantable device, information associated with stored energy of a capacitor included in the implantable device and scheduled energy to be used. In operation 1020, the external device may determine a wireless power quantity to be transmitted to the implantable device based on the received information. In operation 1030, the external device may transmit the determined wireless power quantity to the implantable device. An operation of the external device and an operation of the implantable device may be synchronized.

Figure 11:
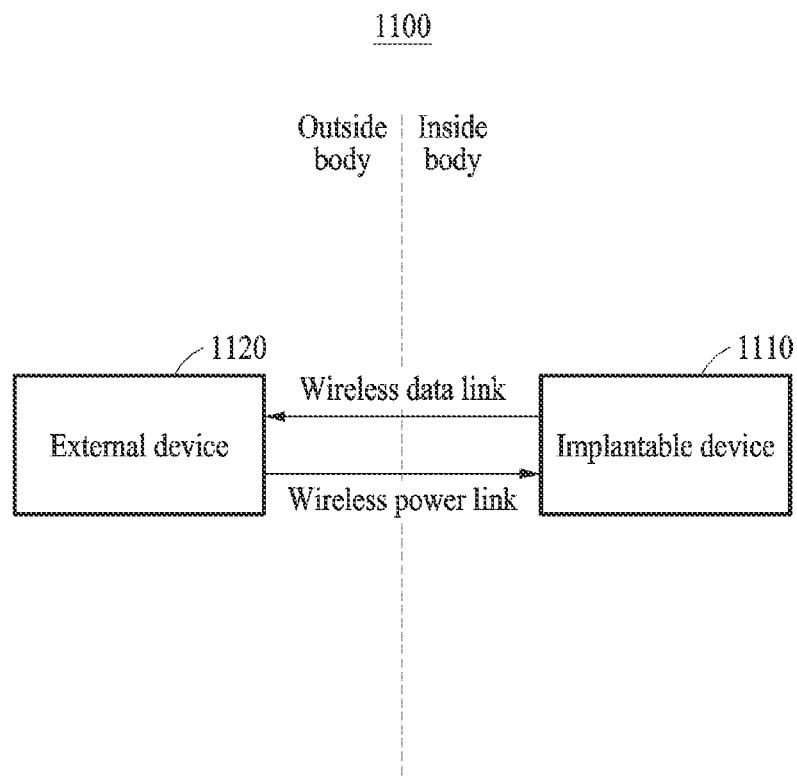
FIG. 11 illustrates an example of a device including an implantable device and an external device.

FIG. 11 illustrates an example of a device including an implantable device and an external device.

Referring to FIG. 11, a device 1100 of one or more embodiments may include an implantable device 1110 (the implantable device 110 of FIG. 1, as a non-limiting example) and an external device 1120 (the external device 120 of FIG. 1, as a non-limiting example).

For a detailed description of the operations described with reference to FIG. 10, reference may be made to what has been described above with reference to FIGS. 1 through 8.

The implantable devices, external devices, matching circuits, PMICs, capacitors, processors, wireless transceivers, neural ICs, controllers, power sources, data modulator-demodulators, implantable device 110, external device 120, implantable device 210, matching circuit 211, PMIC 212, capacitor 213, processor 214, wireless transceiver 215, neural IC 216, external device 220, wireless transceiver 221, controller 222, power source 223, matching circuit 224, implantable device 810, matching circuit 811, PMIC 813, data modulator-demodulator 815, external device 820, data modulator-demodulator 821, power source 823, matching circuit 825, device 1100, implantable device 1110, external device 1120, and other devices, apparatuses, units, modules, and components described herein with respect to FIG. 1-11 are implemented by or representative of hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-11 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents.

What is claimed is:

1. A device comprising:
a wireless power receiver configured to receive wireless power from an external device external to a body;
a capacitor configured to store therein the wireless power received by the wireless power receiver;
a wireless transceiver; and
a processor configured to:
at a previous time, control the wireless transceiver to transmit to the external device information associated with energy stored in the capacitor corresponding to the previous time and energy scheduled for use, at times subsequent to the previous time, by the device when the processor is performing one or more operations of the device; and
at a current time, receive a current energy among the received wireless power, store the current energy in the capacitor, and operate the processor in the performance of the one or more operations using energy stored in the capacitor at the current time, with the one or more operations including a processing of a biosignal of the body,
wherein an operation of the device is synchronized with an operation of the external device, and
wherein a wireless power quantity, of the received wireless power, starting from the current time and during a current time period, has a dependence with the transmitted information.

2. The device of claim 1, wherein performance of the transmitting of the information by the wireless transceiver to the external device and the receiving of the wireless power are synchronized.

3. The device of claim 2, wherein the transmitting of the information and the receiving of the wireless power are synchronized in a current timeslot, corresponding to the current time period, of plural timeslots.

4. The device of claim 1,
wherein the transmission of the information is performed at the previous time in a current timeslot, corresponding to the current time period, based on a determination of the one or more operations to be performed in the current timeslot, and
wherein the wireless power receiver receives the wireless power quantity in the current timeslot.

5. The device of claim 1, wherein the current time is determined by the external device based on the transmitted information.

6. The device of claim 1, wherein the wireless power quantity is dependent on a state change of a wireless power link between the wireless power receiver and the external device.

7. The device of claim 1, wherein, for each of plural timeslots, the wireless power quantity is a quantity that is determined to respectively result in energy, remaining in the capacitor after the operating of the processor in the performance of the one or more operations in a current timeslot, corresponding to the current time period, or at an end of the current timeslot, that corresponds to a preset reference energy.

8. The device of claim 7, wherein, for each of the current timeslots, the preset reference energy is respectively based on a wireless power transfer efficiency that is dependent on the energy stored in the capacitor corresponding to respective previous times.

9. The device of claim 1, wherein a wireless power link for transmitting power to the wireless power receiver is separate from a wireless data link for transmitting information from the wireless transceiver.

10. The device of claim 1, wherein the device is a battery-free device.

11. The device of claim 1, further comprising either one or both of:
a sensor configured to sense the biosignal of the body while the wireless power is not received from the external device; and
a stimulator configured to apply a stimulus to the body while the wireless power is not received.

12. The device of claim 1, wherein the processor is further configured to perform initial booting based on a maximum wireless power transmittable by the external device.

13. The device of claim 1, wherein the device is an implantable device.

14. A system comprising:
the implantable device of claim 13; and
the external device, the external device comprising:
another wireless transceiver configured to receive the transmitted information;
another processor configured to determine the wireless power quantity based on the received information; and
a wireless power transmitter configured to transmit the determined wireless power quantity to the implantable device.

15. The device of claim 1, wherein the scheduled energy comprises energy to be consumed by the processing of the biosignal during the current time period, including times in the current time period subsequent to the transmission of the information to the exterior device and while the wireless power quantity is received by the wireless power receiver.

16. A device comprising:
a wireless transceiver configured to receive, from an implantable device, information associated with stored energy of a capacitor of the implantable device at a previous time and scheduled energy to be used by the implantable device at times subsequent to the previous time;
a wireless power transmitter; and
a processor configured to:
determine a wireless power quantity to be transmitted to the implantable device based on the received information; and
control the wireless power transmitter to transmit the determined wireless power quantity to the implantable device during a current time period, and starting at a current time, for a corresponding operation of the implantable device in a performance of one or more operations using energy stored in the capacitor at the current time,
wherein an operation of the device and an operation of the implantable device are synchronized.

17. The device of claim 16, wherein the receiving of the information and the transmitting of the wireless power are synchronized within a current timeslot of plural timeslots.

18. The device of claim 16, wherein the processor is further configured to determine the current time to perform the transmitting of the wireless power to the implantable device based on the received information.

19. The device of claim 16, wherein, for the determining of the wireless power quantity, the processor is configured to determine the wireless power quantity based further on a determined state change of a wireless power link between the wireless power transmitter and the implantable device.

20. The device of claim 16, wherein the processor is configured to, for each of plural timeslots, determine the wireless power quantity to be a respective quantity that results in energy, remaining in the capacitor after the corresponding operation of the implantable device in the performance of the one or more operations in a current timeslot, corresponding to the current time period, that corresponds to a preset reference energy.

21. The device of claim 16, wherein the device is an external device external to a body.

22. A system, the system comprising:
the external device of claim 21; and
the implantable device, comprising:
a wireless power receiver configured to receive the determined wireless power quantity;
a capacitor configured to store therein the wireless power quantity received by the wireless power receiver;
another wireless transceiver configured to transmit the information to the external device; and
a processor configured to perform the corresponding operation of the implantable device in the performance of one or more operations using energy stored in the capacitor at the current time, with the one or more operations including a processing of a biosignal of the body.

23. A method of operating a device, comprising:
transmitting, to an external device external to a body, information associated with energy in a capacitor of the device at a previous time and scheduled energy to be used at subsequent times for performance of one or more operations by the device;
at a current time, receiving wireless power from the external device and storing the received wireless power in the capacitor, in synchronization with the transmitting of the information that is performed prior to the current time, and performing the one or more operations, wherein one of the one or more operations includes sensing and processing a biosignal of the body using energy stored in the capacitor at the current time, wherein a wireless power quantity of the received wireless power, starting from the current time and during a current time period, has a dependence with the transmitted information.

24. A method of operating a device, comprising:

receiving, from an implantable device, information associated with stored energy of a capacitor of the implantable device at a previous time and scheduled energy to be used by the implantable device at times subsequent to the previous time; and determining a wireless power quantity to be transmitted to the implantable device based on the received information; and transmitting the determined wireless power quantity to the implantable device during a current time period, and starting at a current time, for a corresponding operation of the implantable device in a performance of one or more operations using energy stored in the capacitor at the current time;

wherein an operation of the external device and an operation of the implantable device are synchronized.

25. A device comprising:

a wireless power receiver configured to receive wireless power from an external device external to a body;

a capacitor configured to store therein the wireless power received by the wireless power receiver;

a wireless transceiver configured to transmit, to the external device, information associated with stored energy of the capacitor and scheduled energy to be used; and a processor configured to operate with the stored energy of the capacitor and process a biosignal of the body, wherein an operation of the external device and an operation of the device are synchronized, wherein a wireless power quantity of the wireless power to be received by the wireless power receiver from the external device is determined based on the information transmitted from the wireless transceiver to the external device, and wherein the scheduled energy comprises energy to be consumed by any one or any combination of any two or more of a communicating operation of the wireless transceiver, a biosignal sensing operation, a biosignal processing operation of the processor, and an operation of applying a stimulus to the body.

* * * * *